United States Patent [19]
Motley

[11] Patent Number: 5,641,476
[45] Date of Patent: Jun. 24, 1997

[54] GELLING COMPOSITIONS COMPRISING OPTICALLY ENRICHED GELLANTS

[75] Inventor: Curtis Bobby Motley, Cincinnati, Ohio

[73] Assignee: The Procter & Gamble Company, Cincinnati, Ohio

[21] Appl. No.: 703,618

[22] Filed: Aug. 28, 1996

Related U.S. Application Data

[62] Division of Ser. No. 286,997, Aug. 8, 1994, Pat. No. 5,607,972.

[51] Int. Cl.$^6$ ............................. A61K 7/32; A61K 31/20
[52] U.S. Cl. ............................. 424/65; 514/558; 514/944
[58] Field of Search ............................. 424/65; 514/558, 514/944

[56] References Cited

U.S. PATENT DOCUMENTS

| | | | |
|---|---|---|---|
| 4,502,975 | 3/1985 | Kobayashi et al. | 252/315 |
| 5,298,260 | 3/1994 | Viegas et al. | 424/486 |
| 5,362,494 | 11/1994 | Zysman et al. | 424/401 |

FOREIGN PATENT DOCUMENTS

| | | | |
|---|---|---|---|
| 2-180805 | 7/1990 | Japan | A61K 7/00 |
| 2-264707 | 10/1990 | Japan . | |
| 3-97781 | 4/1991 | Japan . | |
| WO93/23008 | 11/1993 | WIPO | A61K 7/32 |

OTHER PUBLICATIONS

Tachibana et al., "Chiral Mesophases of 12-Hydroxyoctadecanoic Acid in Jelly and in the Solid State. I. A New Type of Lyotropic Mesophase in Jelly with Organic Solvents", *Bull. Chem. Soc. Jpn.* vol. 53, pp. 1714–1719 (1980).
Remington's Pharmaceutical Sciences, 18th ed. p. 1530.
P. Terech, "Small-angle-scattering study of 12-hydroxystearic physical organogels and lubricating greases", 269, *Colloid & Polymer Science*, pp. 490–500 (1991).
McGhie et al., "Conversion of (+)-ricinoleic acid into (–)-ricinoleic acid", Communications to the Editor, Sep. 18, 1982, pp. 719–720, *Chemistry & Industry.*

*Primary Examiner*—Shelley A. Dodson
*Attorney, Agent, or Firm*—John M. Howell; David L. Suter; Milton B. Graff, IV

[57] ABSTRACT

The subject invention relates to low-aqueous gelling compositions comprising optically enriched gellants having the structure:

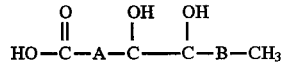

wherein A and B independently represent alkyl groups such that the gellant is an asymmetric, di-chiral, di-hydroxy fatty acid that is about 90% or more in the R, R or S, S form and has from about 6 to about 30 carbon atoms.

7 Claims, No Drawings

GELLING COMPOSITIONS COMPRISING OPTICALLY ENRICHED GELLANTS

This is a division of application Ser. No. 08/286,997, filed on Aug. 8, 1994, U.S. Pat. No. 5,607,972.

FIELD OF THE INVENTION

The subject invention relates to low-aqueous gelling compositions.

BACKGROUND OF THE INVENTION

Organic cosmetic products with different hardness and rheological properties can be achieved by varying the ratio of waxy and/or pasty oils to liquid organic oils in a given composition. In general, these cosmetic products provide good skin feel, but are limited in the amount of liquid oil that can be formulated. These products can also leave visible residue on the skin.

Gels have the ability to retain increased mounts of liquid in a cosmetic composition while significantly reducing or eliminating the visible residue on the skin as compared to a waxy cosmetic of equal hardness. However, one significant disadvantage of typical gel compositions is a tendency of the liquid material to escape or leak from the gel network. This leaking of the liquid material can result in poor gel formation and lower gel stability of any gel which is formed. The leaking may also cause processing difficulties at the temperatures and holding times typically encountered during manufacture.

It is an object of the subject invention to provide low-aqueous gelling compositions with superior gel formation.

SUMMARY OF THE INVENTION

The subject invention involves gelling compositions comprising optically enriched, asymmetric, di-chiral, di-hydroxy fatty acid gellants having adjacent chiral centers.

DETAILED DESCRIPTION OF THE INVENTION

As used herein, the term "alkyl" means carbon-containing chains which may be straight, branched or cyclic; substituted or unsubstituted; saturated, monounsaturated (i.e., one double or triple bond in the carbon chain), or polyunsaturated (i.e., two or more double bonds in the carbon chain, two or more triple bonds in the carbon chain, one or more double and one or more triple bonds in the carbon chain). Unless otherwise indicated, preferred alkyl are as follows. Preferred alkyl are straight or branched chain, more preferably straight chain. Preferred alkyl are unsubstituted, or mono-, di-, or tri- substituted, more preferably monosubstituted or unsubstituted, most preferably unsubstituted. Preferred alkyl are $C_6$ to $C_{30}$, more preferably $C_{10}$ to $C_{28}$ more preferably stiff $C_{14}$ to $C_{24}$ most preferably $C_{22}$.

As used herein, "substituted", in reference to alkyl groups, means such groups that can be mono- or polysubstituted. Preferred substituents are selected from the group consisting of halogen, hydroxy, amino, nitro, carboxy, thio, aryl, alkyl, alkoxy, and aryloxy. More preferred substituents include alkyl, alkoxy and aryl.

As used herein, the term "aryl" means aromatic rings which may be unsubstituted or substituted. Preferred aryl are phenyl or naphthyl, especially phenyl. Preferred aryl are mono-, di- or tri-substituted, or unsubstituted; more preferred aryl are monosubstituted or unsubstituted. Preferred aryl substitutents include alkyl, halo, amino, hydroxy, alkoxy, cyano, nitro and trifluoromethyl.

As used herein, the term "alkoxy" means O-alkyl.
As used herein, the term "aryloxy" means O-aryl.

Gelling Agent

The subject compositions comprise optically enriched gelling agents. The subject gelling agents are asymmetric, linear, branched or cyclic, substituted or unsubstituted, di-chiral, di-hydroxy fatty adds having the structure:

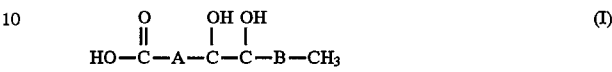

wherein A and B each represent linear, branched or cyclic, saturated or unsaturated, substituted or unsubstituted alkyl having from about 1 to about 13 carbon atoms, preferably from about 3 to about 12 carbon atoms, more preferably from about 5 to about 10 carbon atoms; such that structure (I) represents a di-hydroxy fatty acid having from about 6 to about 30 carbon atoms, more preferably from about 10 to about 24, more preferably still from about 14 to about 22, most preferably about 18 carbon atoms. The two chiral centers in the subject gellants lie in the carbon atoms substituted by the hydroxyl moieties.

Preferred gellants include 9,10-dihydroxystearic add, 13,14-dihydroxystearic acid, 13,14-dihydroxydocosanoic add, and 11,12-dihydroxystearic acid. The most preferred gellant is 13,14-dihydroxydocosanoic acid.

As used herein, the term "optically enriched" means that the gelling agent contains about 90% or more, preferably about 95% or more, more preferably 98% or more, most preferably about 100% of a given stereoisomer (i.e. intramolecularly, both chiral centers are R or both chiral centers are S). Thus, the gelling agent contains less than about 10%, preferably less than about 5%, more preferably less than about 2%, most preferably 0%, of the racemic form (R, S or S, R stereochemistry within the same molecule). It has been unexpectedly found that when an optically enriched sample of gellant is used in the subject invention, superior gelling results. While not limited to any particular mechanism of action, it is believed that the optically enriched gellant is thermodynamically favored to form fibrils that are aligned and bundle, thereby contributing to a more ordered macrostructure in which the liquid base is trapped. The racemic mixture, on the other hand, is thermodynamically favored to form large crystals.

Mixtures of optically enriched gelling agents are also effective in the subject invention.

The subject compositions preferably comprise from about 0.1% to about 25%, more preferably from about 1% to about 15%, more preferably still from about 3% to about 12%, most preferably from about 4% to about 10% of the gellant.

Liquid Base Material

The subject compositions also comprise a liquid base material. A liquid base matrix is formed by combining the gelling agent with a liquid base material. As used herein, the term "liquid" refers to materials which are liquids at ambient conditions and the term "liquid base material" includes all liquids within the composition.

The liquid base material of the subject invention is preferably used at levels from about 10% to about 95% of the subject compositions; and more preferably from about 45% to about 80%. The liquid base material preferably includes a volatile, non-polar, oil and a non-volatile, relatively polar co-solvent.

The term "non-polar" typically means that the solution has a solubility parameter below about 6.5. The term "volatile" as used herein refers to materials which exhibit a vapor pressure of more than about 2 mm Hg at 25° C. at one atmosphere and/or to materials which have a boiling point at one atmosphere of at less than about 300° C. The non-polar, volatile oil tends to impart highly desirable aesthetic properties to the gel and is preferably used at levels from about 10% to about 70% of the composition; more preferably, from about 25% to about 60%; more preferably from about 40%, to about 60%.

Particularly useful non-polar, volatile oils include silicone oils, hydrocarbons, and mixtures thereof. Such non-polar, volatile oils are disclosed, for example, in Cosmetics, Science, and Technology, Vol. 1, 27–104 edited by Balsam and Sagarin, 1972, incorporated herein by reference. The non-polar, volatile oils useful in the present invention may be saturated or unsaturated, straight or branched chained, aliphatic or aromatic. Preferred non-polar, volatile hydrocarbons include isodecane (such as Permethyl-99A®, available from Presperse Inc.) and the $C_7$–$C_8$ through $C_{12}$–$C_{15}$ isoparaffins (such as the Isopar® Series available from Exxon Chemicals).

Non-polar, volatile silicone oils are highly preferred because they provide the gel with highly desirable aesthetics. Non-polar, volatile liquid silicone oils are disclosed in U.S. Pat. No. 4,781,917 issued to Luebbe et al., on Nov. 1, 1988; and in Todd et al., "Volatile Silicone Fluids for Cosmetics", Cosmetics and Toiletries, 91:27–32 (1976); both incorporated herein by reference. Particularly preferred volatile silicone oils include cyclic volatile silicones corresponding to the formula:

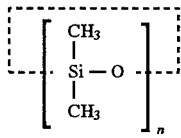

wherein n is from about 3 to about 7; and linear volatile silicones corresponding to the formula:

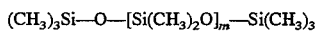

wherein m is from about 1 to about 7. Linear volatile silicones generally have a viscosity of less than about 5 centistokes at 25° C., whereas the cyclic silicones have viscosities of less than about 10 centistokes at 25° C. Highly preferred examples of volatile silicone oils include cyclomethicones of varying viscosities, e.g., Dow Corning200®, Dow Corning 244®, Dow Corning 245®, Dow Corning 344®, and Dow Corning 345®, (commercially available from Dow Corning Corp.); SF-1204®and SF-1202® Silicone Fluids (commercially available from G. E. Silicones), GE 7207® and 7158® (commercially available from General Electric Co.); and SWS-03314® (commercially available from SWS Silicones Corp.).

The phrase "relatively polar" as used herein means more polar than another material in terms of solubility parameter, i.e., the higher the solubility parameter the more polar the liquid. The non-volatile co-solvent is "relatively polar" as compared to the non-polar, volatile oil discussed above. Therefore, the non-volatile co-solvent is more polar (i.e., has a higher solubility parameter) than at least one of the non-polar, volatile oils. The relatively polar co-solvent of the subject invention aids in the utilization of reduced processing temperatures by solubilizing the gellant and being soluble in the non-polar, volatile oil when subjected to reduced processing temperatures. In addition to enabling reduced processing temperatures, the co-solvent enables the inclusion of greater amounts of the non-polar, volatile oil. This is advantageous because, as discussed above, the non-polar, volatile oil provides significant cosmetic benefits.

The quantity of relatively polar, non-volatile co-solvent is preferably kept to a minimum because it tends to adversely affect product cosmetics. The relatively polar, non-volatile co-solvent is preferably included at levels from about 2% to about 60% of the composition; more preferably from about 5% to about 25%; and most preferably from about 7% to about 20%.

Relatively polar, non-volatile liquids useful as the co-solvent in the subject invention are disclosed, for example, in Cosmetics, Science, and Technology, Vol. 1, 27–104 edited by Balsam and Sagarin, 1972; U.S. Pat. No. 4,202,879 issued to Shelton on May 13, 1980; and U.S. Pat. No. 4,816,261 issued to Luebbe et al. on Mar. 28, 1989; all incorporated herein by reference. Relatively polar, non-volatile co-solvents useful in the subject invention preferably include silicone oils; hydrocarbon oils; fatty alcohols; fatty acids; esters of mono and dibasic carboxylic acids with mono and polyhydric alcohols; polyoxyethylenes; polyoxypropylenes; mixtures of polyoxyethylene and polyoxypropylene ethers of fatty alcohols; and mixtures thereof. The relatively polar, non-volatile co-solvents useful in the subject invention may be either saturated or unsaturated, have an aliphatic character and be straight or branched chained or contain aliphatic rings or aromatic rings.

More preferably, the relatively polar, non-volatile liquid co-solvents include fatty alcohols having from about 12–26 carbon atoms; fatty acids having from about 12–26 carbon atoms; esters of monobasic carboxylic adds and alcohols having from about 14–30 carbon atoms; esters of dibasic carboxylic acids and alcohols having from about 10–30 carbon atoms; esters of polyhydric alcohols and carboxylic acids having from about 5–26 carbon atoms; ethoxylated, propoxylated, and mixtures of ethoxylated and propoxylated ethers of fatty alcohols with from about 12–26 carbon atoms and a degree of ethoxylation and propoxylation of below about 50; and mixtures thereof.

More preferred relatively polar, non-volatile liquid co-solvents include propoxylated ethers of $C_{14}$–$C_{18}$ fatty alcohols having a degree of propoxylation below about 50, esters of $C_2$–$C_8$ alcohols and $C_{12}$–$C_{26}$ carboxylic acids (e.g. ethyl myristate, isopropyl palmitate), esters of $C_{12}$–$C_{26}$ alcohols and benzoic acid (e.g. Finsolv TN supplied by Finetex), diesters of $C_2$–$C_8$ alcohols and adipic, sebacic, and phthalic acids (e.g., diisopropyl sebacate, diisopropyl adipate, di-n-butyl phthalate), polyhydric alcohol esters of $C_6$–$C_{26}$ carboxylic acids (e.g., propylene glycol dicaprate/dicaprylate, propylene glycol isostearate); and mixtures thereof.

Even more preferred relatively polar, non-volatile liquid co-solvents include branched-chain aliphatic fatty alcohols having from about 12–26 carbon atoms, such as isocetyl alcohol, octyldecanol, octyldodecanol and undecylpentadecanol. Octyldodecanol is most preferred. Such preferred aliphatic fatty alcohols are particularly useful in combination with the volatile liquid silicone oils discussed herein to adjust the average solubility of the liquid base material.

In addition to the liquids discussed above, the liquid base material may optionally include non-volatile, non-polar emollients which tend to improve product cosmetics. Typical non-volatile, non-polar emollients are disclosed, for example, in Cosmetics, Science, and Technology, Vol. 1, 27–104 edited by Balsam and Sagarin, 1972; U.S. Pat. No. 4,202,1379 issued to Shelton on May 13, 1980; and U.S. Pat. No. 4,816,261 issued to Luebbe et al. on Mar. 28, 1989; all incorporated herein by reference. The non-volatile silicone oils useful in the present invention are essentially non-volatile polysiloxanes, paraffinic hydrocarbon oils, and mixtures thereof. The polysiloxanes useful in the subject invention include polyalkylsiloxanes, polyarylsiloxanes, polyalkylarylsiloxanes, polyethersiloxane copolymers, and mixtures thereof. Examples of these include polydimethyl siloxanes having viscosities of from about 5 to about 100,000 centistokes at 25° C.

Among the preferred non-volatile silicone emollients useful in the subject compositions are the polydimethyl siloxanes having viscosities from about 2 to about 400 centistokes at 25° C. Such polyalkylsiloxanes include the Viscasil® series (sold by General Electric Company) and the Dow Corning 200® series (sold by Dow Corning Corp.). Polyalkylarylsiloxanes include polymethylphenyl siloxanes having viscosities of from about 15 to about 65 centistokes at 25° C. These are available, for example, as SF 1075 methyl-phenyl fluid® (sold by General Electric Company) and 556 Cosmetic Grade Fluid® (sold by Dow Corning Corp.). Useful poly-ethersiloxane copolymers include, for example, a polyoxyalkylene ether copolymer having a viscosity of about 1200 to 1500 centistokes at 25° C. Such a fluid is available as SF1066® organosilicone surfactant (sold by General Electric Company). Polysiloxane ethylene glycol ether copolymers are preferred copolymers for use in the subject compositions.

Non-volatile paraffinic hydrocarbon oils useful in the subject invention include mineral oils and certain branched-chain hydrocarbons. Examples of these fluids are disclosed in U.S. Pat. No. 5,019,375 issued to Tanner et al. on May 28, 1991, incorporated herein by reference. Preferred mineral oils have the following properties: viscosity from about 5 centistokes to about 70 centistokes at 40° C.; density between about 0.82 and 0.89 g/cm$^3$ at 25° C.; flash point between about 138° C. and about 216° C.; and carbon chain length between about 14 and about 40 carbon atoms.

Preferred branched chain hydrocarbon oils have the following properties: density between about 0.79 and about 0.89 g/cm$^3$ at 20° C.; boiling point greater than about 250° C.; and flash point between about 110° C. and about 200° C.

Particularly preferred branched-chain hydrocarbons include Permethyl 103A®, which contains an average or about 24 carbon atoms; Permethyl 104A®, which contains an average of about 68 carbon atoms; Permethyl 102A®, which contains an average of about 20 carbon atoms; all of which may be purchased from Permethyl Corporation; and Ethylflo 364® which contains a mixture of 30 carbon atoms and 40 carbon atoms and may be purchased from Ethyl Corp.

The liquid base materials include emollients which have a solubility parameter from about 5 to about 9. It is preferable that, in aggregate, the average solubility parameter of the liquid base material be from about 6 to about 9. Hence, a mixture of emollients may be used as the liquid base material herein, each having a solubility parameter in the range of from about 5 to about 9, such that the average solubility parameter of the mixture is from about 6 to about 9. Solubility parameters are common to the art of antiperspirant stick formulation and the means to determine them are disclosed by C. D. Vaughan, "Solubility Effects in Product, Package, Penetration and Preservation" 103 Cosmetics and Toiletries 47–69, October 1988; and C. D. Vaughan, "Using Solubility Parameters in Cosmetics Formulation", 36 *J Soc. Cosmetic Chemists* 319–333, September/October, 1985; both incorporated herein by reference.

The liquid base material comprises at least two solvents. One solvent is preferably a silicone oil. The second solvent is preferably an organic solvent with a solubility parameter of less than 9.

It is important that the liquid base material be of a type, and used at a level sufficient to solubilize the gelling agent when heated, to permit substantially uniform mixing. The liquid base material must be compatible with the gelling agent so that the mixture of the two remains homogeneous and does not phase separate during manufacturing and so that the finished product remains homogeneous and does not phase separate at ambient conditions over the normal shelf-life which may be upwards of one year. Furthermore, the liquid base materials are typically selected to provide aesthetic benefits, such as emolliency, low tack and/or minimized visible residue, without significant interference with other components of the formulation. The particular liquid base material should be safe for application to human skin.

As used herein, the term "gel" means a non free flowing solid after the gellant has been melted and allowed to cool to ambient temperature.

As used herein, the term "low-aqueous gel composition" means a gel composition comprising less than 50% water, preferably less than 30%, more preferably less than 20% water, even more preferably less than 10% water, also preferably less than 5% water. The most preferred gel compositions are substantially water free. As used herein, the term "substantially water free" means that the only water content in the formulation comes from the degrees of hydration associated with the raw materials used in the formulation.

Optional Ingredients

Gel compositions of the subject invention may contain optional components which act as additional actives or modify the physical characteristics of the composition or the components making up the compositions. Such components are well known in the art. A non-limiting group of these optional components include colorants, perfumes, thickeners, distributing agents, emulsifiers, bacteriostats, fungistats, and mixtures thereof. Optional components useful herein are described in the following references: U.S. Pat. No. 4,049,792 issued to Elsnau on Sep. 20, 1977; Canadian Patent 1,164,347 which issued to Beckmeyer et al. on Mar. 27, 1984; European Patent Application 117,070 which published on Aug. 29, 1984; and Geria, "Formulation of Stick Antiperspirants and Deodorants", *Cosmetics and Toiletries*, 99:55–60 (1984); all incorporated herein by reference.

Emulsifiers are particularly useful in the subject invention. The level of emulsifiers used in the subject invention is typically less than about 10% of the composition, preferably less than about 5%. These emulsifiers include non-ionic surfactants useful for forming water-in-oil emulsions. Examples of these emulsifiers include polyoxyethylene ethers of fatty alcohols, and polyoxyethylene-polysiloxane copolymers. Such emulsifiers are disclosed by EPO Application 373,424 Raleigh et al., and U.S. Ser. No. 530,671, Cedeno et al., filed Jul. 2, 1991; incorporated herein by reference.

Thickeners are also useful in the subject invention. Typically, thickeners comprise less than about 5% of the composition. Examples of thickeners useful in the subject compositions are disclosed in U.S. Pat. No. 4,985,238, Tanner et al., issued Jan. 15, 1991; incorporated herein by reference. These thickeners include wax-like materials such as beeswax, cerasin, hydrogenated castor oil, synthetic waxes such as Fisher Tropsch® waxes, microcrystalline waxes, polyethylene waxes, and mixtures thereof. Particulate thickeners, such as clay and silica, are also useful.

Particulate and filler materials may also be included in the subject compositions. These materials are typically used at levels from about 0.5% to about 5% of the composition, preferably not more than 3%. Such materials are disclosed in U.S. Pat. No. 5,019,375, Tanner et al., issued May 28, 1991; incorporated herein by reference. Suitable filler materials include collodial silica (such as Cab-O-Sil®, sold by Cabot Corp.), clays (such as bentonite), hydrophobic (quaternized) clays, silica/alumina thickeners, silicate powders such as talc, alumina silicate, and magnesium silicate, modified corn starches, metallic stearates, and mixtures thereof. The use of such fillers as stabilizing agents in cosmetic sticks is disclosed in U.S. Pat. No. 4,126,679, Davy et al., issued Nov. 21, 1987; incorporated herein by reference. Examples of other particulate materials include particulate hydrophilic polymers such as cellulose ether polymers, modified starches, polyamides, and polypeptides.

A wash-off agent may be utilized to improve the ease with which the ingredients, particularly the gelling agent and the non-polar, non-volatile oils, may be washed off. The wash-off agent is preferably a non-liquid. The wash-off agent is typically in the gel in an amount from about 0.1% to about 10% of the composition.

Typical wash-off agents are non-liquids selected from the group consisting of polyoxyethylene ethers having the formula $R_1(OCH_2CH_2)_nOH$; polyoxyethylene esters having the formula $R_1CO(OCH_2CH_2)_nOH$; polyoxyethylene glyceryl esters having the formula $(R_1COO)CH_2CH(OH)CH_2(OCH_2CH_2)_nOH$ or having the formula $HOCH_2CH(OOCR_1)CH_2(OCH_2CH_2)_nOH$; and polyoxyethylene glyceryl diesters having the formula $R_1COOCH_2CH(OOCR_2)CH_2(OCH_2CH_2)_nOH$, preferably, the polyoxyethylene ethers, wherein $R_1$ and $R_2$ are, independently, alkyl, alkenyl, or aromatic hydrocarbon which may be substituted or unsubstituted, preferably an alkyl radical, having from about 4 to about 22 carbon atoms; and n is from about 2 to about 80.

Preferred examples of such wash-off agents include: ceteth-2 through ceteth-30, steareth-2 through steareth-30, ceteareth-2 through ceteareth-30, PEG-2 stearate through PEG-30 stearate, PEG-12 isostearate, PEG-16 hydrogenated castor oil, PEG-40 hydrogenated castor oil, Unithox-480®, Unithox-425®, and PEG-20 glyceryl stearate; more preferably, ceteareth-20, steareth-21, PEG-20 stearate, Unithox-480®, Unithox-425®, and PEG-16 hydrogenated castor oil; more preferably still, ceteareth-20, Unithox-480® and Unithox-425®; also preferably Unithox-480® and Unithox-425®.

Antiperspirants

The subject gels are particularly useful for antiperspirant and/or deodorant compositions. Such compositions contain an astringent antiperspirant active. Antiperspirant actives useful in the subject invention are well known in the art. See e.g. "Antiperspirants and Deodorants", *Cosmetic Science and Technology Series*, K. Laden & C. Felger, eds., Vol. 7., pp. 42–56 (1988); incorporated herein by reference. These actives are used at levels from about 0.5% to about 60% of the composition, preferably from about 5% to about 35%, of the gel stick composition. These weight percentages are calculated on an anhydrous metal salt basis (exclusive of complexing agents).

Any aluminum astringent antiperspirant salt or aluminum and/or zirconium astringent complex can be employed herein. Salts useful as astringent antiperspirant salts or as components of astringent complexes include aluminum halides, aluminum hydroxy-halides, zirconyl oxyhalides, zirconyl hydroxy-halides, and mixtures of these materials.

Aluminum salts of this type include aluminum chloride and the aluminum hydroxyhalides having the general formula $Al_2(OH)_xQ_y\cdot XH_2O$ wherein:

(a) Q is chlorine, bromine or iodine;

(b) x is from about 2 to about 5, and x+y=about 6, and x and y do not need to be integers; and (c) X is from about 1 to about 6.

Aluminum salts of this type can be prepared in the manner described more fully in U.S. Pat. No. 3,887,692 issued to Gilman on Jun. 3, 1975, and U.S. Pat. No. 3,904,741 issued to Jones and Rubino on Sep. 9, 1975; both incorporated herein by reference.

The zirconium compounds which are useful in the present invention include both the zirconium oxy salts and zirconium hydroxy salts, also referred to as the zirconyl salts and zirconyl hydroxy salts. These compounds may be represented by the following general empirical formula:

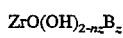

$$ZrO(OH)_{2-nz}B_z$$

wherein:

(a) z may vary from about 0.9 to about 2 and need not be an integer, (b) n is the valence of B;

(c) 2−nz is greater than or equal to 0:

(d) B is selected from the group consisting of halides, nitrate, sulfamate, sulfate, and mixtures thereof.

Although only zirconium compounds are exemplified in this specification, other Group IVB metal compounds, including hafnium, can be used in the subject invention.

As with the basic aluminum compounds, the above formula is greatly simplified and is intended to represent and include compounds having coordinated and/or bound water in various quantities, as well as polymers, mixtures and complexes of the above. As will be seen from the above formula, the zirconium hydroxy salts actually represent a range of compounds having various amounts of the hydroxy group, varying from about 1.1 to only slightly greater than zero groups per molecule.

Several types of antiperspirant complexes utilizing the above antiperspirant salts are known in the art. For example, U.S. Pat. No. 3,792,068 issued to Luedders et al. on Feb. 12, 1974 discloses complexes of aluminum, zirconium and amino acids, such as glycine. Complexes such as those disclosed in the Luedders et al. patent and other similar complexes are commonly known as ZAG. ZAG complexes are chemically analyzable for the presence of aluminum, zirconium and chlorine. ZAG complexes useful herein are identified by the specification of both the molar ratio of aluminum to zirconium (hereinafter "Al:Zr" ratio) and the molar ratio of total metal to chlorine (hereinafter "Metal:Cl" ratio). ZAG complexes useful herein have an Al:Zr ratio of from about 1.67 to about 12.5 and a Metal:Cl ratio of from about 0.73 to about 1.93.

Preferred ZAG complexes are formed by (A) co-dissolving in water (1) one part $Al_2(OH)_{6-m}Q_m$, wherein Q is an anion selected from the group consisting of chloride, bromide and iodide, and m is a number from about 0.8 to about 2.0;

(2) x parts $ZrO(OH)_{2-a}Q_a\cdot nH_2O$, where Q is chloride, bromide or iodide; where a is from about 1 to about 2; where n is from about 1 to about 8; and where x has a value of from about 0.16 to about 1.2;

(3) p parts neutral amino acid selected from the group consisting of glycine, dl-tryptophane, dl-b-phenylalanint, dl-valine, dl-methionine and b-alanine, and where p has a value of from about 0.06 to about 0.53;

(B) co-drying the resultant mixture to a friable solid; and (C) reducing the resultant dried inorganic-organic antiperspirant complex to particulate form.

A preferred aluminum compound for preparation of such ZAG type complexes is aluminum chlorhydroxide of the empirical formula $Al_2(OH)_5Cl.2H_2O$. Preferred zirconium compounds for preparation of such ZAG-type complexes are zirconyl hydroxychloride having the empirical formula $ZrO(OH)Cl.3H_2O$ and the zirconyl hydroxyhalides of the empirical formula $ZrO(OH)_{2-a}Cl_2nH_2O$ wherein a is from about 1.5 to about 1.87, and n is from about 1 to about 7. The preferred amino acid for preparing such ZAG-type complexes is glycine of the formula $CH_2(NH_2)COOH$. Salts of such amino acids can also be employed in the antiperspirant complexes. See U.S. Pat. No. 4,017,599 issued Apr. 12, 1977, to Rubino; incorporated herein by reference.

A wide variety of other types of antiperspirant complexes are also known in the art. For example, U.S. Pat. No. 3,903,258 issued to Siegal on Sep. 2, 1975 discloses a zirconium aluminum complex prepared by reacting zirconyl chloride with aluminum hydroxide and aluminum chlorhydroxide. U.S. Pat. No. 3,979,510 issued to Rubino on Sep. 7, 1976 discloses an antiperspirant complex formed from certain aluminum compounds, certain zirconium compounds, and certain complex aluminum buffers. U.S. Pat. No. 3,981,896 issued to Pauling on Sep. 21, 1976 discloses an antiperspirant complex prepared from an aluminum polyol compound, a zirconium compound and an organic buffer. U.S. Pat. No. 3,970,748 issued to Mecca on Jul. 20, 1976 discloses an aluminum chlorhydroxy glycinate complex of the approximate general formula $[Al_2(OH)_4Cl][H_2CNH_2COOH]$.

Of all the above types of antiperspirant actives, preferred compounds include the 5/6 basic aluminum salts of the empirical formula $Al_2(OH)_5Cl.2H_2O$; mixtures of $AlCl_3.6H_2O$ and $Al_2(OH)_5Cl.2H_2O$ with aluminum chloride to aluminum hydroxychloride weight ratios of up to about 0.5; ZAG type complexes wherein the zirconium salt is $ZrO(OH)Cl.3H_2O$, the aluminum salt is $Al_2(OH)_5Cl.2H_2O$ or the aforementioned mixtures of $AlCl_3.6H_2O$ and $Al_2(OH)_5Cl.2H_2O$ wherein the total metal to chloride molar ratio in the complex is less than about 1.25 and the Al:Zr molar ratio is about 3.3, and the amino acid is glycine; and ZAG-type complexes wherein the zirconium salt is $ZrO(OH)_{2-a}Cl_a.nH_2O$ wherein a is from about 1.5 to about 1.87 and n is from about 1 to about 7, the aluminum salt is $Al_2(OH)_5Cl.2H_2O$, and the amino acid is glycine.

The active may be incorporated either in solubilized or particulate form. Reduction in the amount of interaction between the antiperspirant active and the gelling agent results in better gel stick compositions. This interaction can he reduced by decreasing the surface area of the antiperspirant active; thereby reducing the interaction sites. The antiperspirant active is preferably in particulate form wherein the surface area of the active is relatively low. The surface area of the antiperspirant active can be reduced by increasing the size and density of the active particles. The particulate antiperspirant active preferably has a density which is greater than about 0.7 $g/cm^3$ and an average particle size (as measured by a Coulter Multisizer 11 manufactured by Coulter Corporation, Haleah, Fla.) greater than about 10 microns; more preferably, greater than about 30 microns; and most preferably, greater than about 40 microns. Such preferred materials can be purchased from Westwood Chemical Company, Middletown, N.Y. under the trade name Westchlor ZR. Suitable antiperspirant actives are disclosed, for example, in U.S. Pat. No. 4,147,766 which issued on Apr. 3, 1979 to Kozischek.

Solubilized antiperspirant actives which may be utilized in the subject invention are also well known in the art. These materials utilize monohydric or polyhydric alcohols or water to solublize the antiperspirant active before it is incorporated into the product. The levels of these polar solvents is less than 25%, and preferably less than 15% of the composition. Examples of such actives are taught, for example, in U.S. Pat. No. 4,137,306 issued to Rubino on Jan. 30, 1979; U.S. patent application Ser. No. 370,559, Smith and Ward, filed Jun. 23, 1989; and European Patent Application 0295070 published Dec. 14, 1988; all incorporated herein by reference.

METHODS OF MANUFACTURE

The subject compositions may be manufactured by typical methods known to those skilled in the art. See, e.g., *Gels and Sticks Formulary*, 99 Cosmetics & Toiletties 77–84, 1984; incorporated herein by reference. The following method is particularly preferred.

The gelling agent and the liquid base material are combined in a vessel equipped with a heat source. The mixture is heated to between about 80° C. and about 140° C. with stirring until a homogeneous, molten solution is formed. Preferably, the homogeneous, molten solution is allowed to cool to a mixing temperature, typically between about 65° C. and about 120° C. Alternatively, the mixture is heated to the mixing temperature until the mixture forms a homogeneous, molten solution. This alternative method, however, typically takes longer than overheating and cooling.

In case of antiperspirants, the active and optional ingredients, such as fragrances and colors, are added into the homogeneous molten solution in the above vessel with stirring. The mixture is cooled until thickening occurs and poured into containers.

EXAMPLES

The following examples further describe and demonstrate embodiments within the scope of the subject invention. These examples are solely for the purpose of illustration and are not to be construed as limitations of the present invention as many variations are possible without departing from the spirit or scope thereof.

The levels of the components in the examples below are expressed by total weight of the composition.

weight of the composition.

| Ingredient | EXAMPLE NO. | | | | | | | |
|---|---|---|---|---|---|---|---|---|
| | 1 | 2 | 3 | 4 | 5 | 6 | 7 | 8 |
| 11,12 di-hydroxystearic acid (S,S isomer) | — | 2 | 1 | 5 | 7 | — | 6 | — |
| 11,12 di-hydroxystearic acid (R,R isomer) | 2 | 3 | 4 | 1 | — | 3 | — | 1 |
| Cyclomethicone D-5[1] | q.s. | q.s. | q.s. | q.s. | q.s. | q.s. | q.s. | q.s. |
| Polyphenylmethyl-siloxane[2] | — | — | — | 3 | — | — | 5 | — |
| Light mineral oil[3] | 2 | — | — | — | — | — | — | — |
| Panalane-L-14E ®[4] | — | 15 | 10 | 11 | — | — | — | — |
| Isopropyl Myristate | — | 15 | 15 | 16 | — | — | 11 | — |
| Isopropyl Alcohol | — | — | — | — | 18 | — | — | — |
| Captex 200 ®[5] | — | — | — | — | — | 15 | — | — |
| $C_{12}$-$C_{15}$ Alcohols Benzoate[6] | — | — | — | — | — | — | 8 | — |
| PPG-3 Myristyl Ether | — | — | — | — | — | — | — | 26 |
| Diisopropyl Sebacate[7] | 43 | — | — | — | — | — | — | — |
| Aluminum Zirconium Trichlorhydrex Gly ®[8] | 25 | — | — | 20 | — | 40 | 25 | — |
| Aluminum Chlorohydrate[9] | — | — | — | — | 30 | — | — | — |
| EDTA | 0.2 | 0.1 | 0.5 | 1 | 5 | 10 | 7 | 0.01 |
| Talc | 3 | — | — | 2 | — | — | — | 5 |

[1]Dow Corning 245 Fluid ®-cyclic polydimethylsiloxane
[2]Dow Corning 556 Fluid ®
[3]Benol White Mineral Oil supplied by Witco Chemical Corp.
[4]polyisobutene supplied by Amoco Chemical Company
[5]propylene glycol dicaprate/dicaprylate supplied by Capital City Products
[6]Finsolv TN ® supplied by Finetex
[7]Schercemol DIS ® supplied by Scher Chemicals Inc.
[8]Supplied by Westwood Chemical Co.
[9]Westchlor DM200 ® supplied by Westwood Chemical Co.

| Ingredient | EXAMPLE NO. | | | | | | | | | |
|---|---|---|---|---|---|---|---|---|---|---|
| | 9 | 10 | 11 | 12 | 13 | 14 | 15 | 16 | 17 | 18 |
| 13,14-dihydroxydocosanoic acid (S,S isomer) | 6 | 6 | 6 | 6 | 6 | 6 | 6 | 6 | 6 | 6 |
| Cyclomethicone D4[1] | q.s. | — | q.s. | — | q.s. | q.s. | q.s. | q.s. | — | — |
| Cyclomethicone D-5[2] | — | q.s. | — | q.s. | — | — | — | — | q.s. | q.s. |
| PPG-3-myristyl ether | — | — | — | — | — | 12 | — | — | — | — |
| PPG-5-butyl ether | — | — | — | — | — | — | 10.5 | — | — | — |
| PPG-10-cetyl ether | — | — | — | — | — | — | — | 12.5 | — | — |
| Isocetyl alcohol | 7 | 8 | 13 | — | — | — | — | — | — | — |
| Isostearyl alcohol | — | — | — | 13 | — | — | — | — | — | — |
| Octyldodecanol | — | — | — | — | 8.5 | — | — | — | 14 | 14 |
| Polydecene[3] | — | — | 26 | — | — | — | — | — | — | — |
| Citric Acid | 4 | 1 | 10 | 0.1 | 2 | 5 | 0.2 | 0.5 | 0.01 | 0.05 |
| Ceteareth-20 | — | — | — | — | — | — | — | — | 2.5 | 2.5 |
| Dipropyleneglycol | — | — | — | — | — | — | — | — | — | 0.25 |
| $C_{20-40}$ alcohols[4] | — | — | — | — | — | — | — | — | 0.5 | 0.5 |

[1]Dow Corning 245 Fluid ® - cyclic polydimethylsiloxane
[2]Dow Corning 244 Fluid ® - cyclic polydimethylsiloxane
[3]Ethylflo 364 ® supplied by Ethyl Corp.
[4]Unilin 425 ® supplied by Petrolite

| Ingredient | EXAMPLE 19 |
|---|---|
| Octyldodecanol | 14 |
| 6,7 dihydroxystearic acid (S,S isomer) | 7 |
| Unithox 480 ® | 1.25 |
| Unithox 425 ® | 0.5 |
| Aluminum Zirconium Trichlorohydrex Gly ®[1] | 26 |
| Cyclomethicone D-5[2] | q.s. |

[1]Supplied by Westwood Chemical Co.
[2]Dow Corning 245 Fluid ® - cyclic polydimethylsiloxane

| Ingredient | EXAMPLE 20 | EXAMPLE 21 |
|---|---|---|
| $C_{12}$-$C_{15}$ Alcohols Benzoate (Finsolv TN ®) | 30 | 30 |
| Cyclomethicone D-5 | q.s. | q.s. |
| 11,12 dihydroxystearic acid (S,S isomer) | 10 | 10 |
| Aluminum Zirconium Trichlorohydrex Gly ® | 26 | — |

-continued

| Ingredient | EXAMPLE 22 |
|---|---|
| 13,14-dihydroxydocosanoic acid (R,R isomer) | 5 |
| Triclosan | 0.3 |
| Perfume | 0.1 |
| Cyclomethicone D-5 | q.s. |
| $C_{12}$–$C_{15}$ Alcohols Benzoate (Finsolv TN ®) | 33.1 |

| Ingredient | EXAMPLE 23 |
|---|---|
| 11,12-dihydroxystearic acid (R,R isomer) | 4 |
| 9,10-dihydroxystearic acid (R,R isomer) | 1 |
| Triclosan | 0.3 |
| Perfume | 0.1 |
| Cyclomethicone D-5 | q.s. |
| $C_{12}$–$C_{15}$ Alcohols Benzoate (Finsolv TN ®) | 33.1 |

What is claimed is:

1. A low-aqueous antiperspirant gel composition comprising:
   a) an effective amount of an antiperspirant active;
   b) a sufficient amount of an optically enriched gellant to form a gel wherein said gellant has the structure:

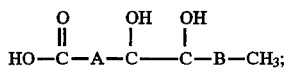

wherein A and B independently represent linear, branched or cyclic, saturated or unsaturated, substituted or unsubstituted alkyl groups wherein the substituents are selected from the group consisting of halogen, hydroxyl, amino, nitro, carboxy, thio aryl, alkyl, alkoxy, aryloxy groups and mixtures thereof, such that the gellant is an asymmetric, di-chiral, di-hydroxy fatty acid that is about 90% or more in the R, R or S, S form and has from about 6 to about 30 carbon atoms; and
   c) a sufficient amount of a liquid base material, liquid at ambient conditions, selected from the group consisting of volatile and non-polar oils, non-volatile and relatively polar co-solvents and mixtures thereof.

2. The composition of claim 1 wherein:
   a) A and B each represent linear or branched alkyl having from about 3 to about 12 carbon atoms;
   b) the gellant has from about 10 to about 28 carbon atoms and is about 95% or more in the R, R or S, S form; and
   c) the active is a complex of aluminum, zirconia and amino acids.

3. The composition of claim 2 wherein A and B represent unsubstituted alkyl or substituted alkyl wherein any substituent is selected from the group consisting of halogen, hydroxy, amino, nitro, carboxy, thio, akyl, alkyl, alkoxy and aryloxy.

4. The composition of claim 3 wherein A and B each represent linear, saturated alkyl which are unsubstituted or substituted, any substituent being selected from the group consisting of alkyl, alkoxy and aryl.

5. The composition of claim 4 wherein the composition is substantially water free and is about 98% or more in the R, R or S, S form.

6. The composition of claim 5 wherein the liquid base material comprises at least two solvents.

7. The composition of claim 6 wherein the gellant has about 22 carbon atoms, and is about 100% in the R, R or S, S form.

* * * * *

UNITED STATES PATENT AND TRADEMARK OFFICE
CERTIFICATE OF CORRECTION

PATENT NO. : 5,641,476
DATED : June 24, 1997
INVENTOR(S) : Curtis B. Motley

It is certified that error appears in the above-identified patent and that said Letters Patent is hereby corrected as shown below:

At column 1, line 19 "mounts" should read --amounts--.
At column 1, line 54 "preferably stiff" should read --preferably still--.
At column 2, line 8 "adds" should read --acids--.
At column 2, line 24 "add" should read --acid--.
At column 2, line 26 "add" should read --acid--.
At column 3, line 9 "40%, to about" should read --40% to about--.
At column 4, line 31 "adds" should read --acids--.
At column 4, line 66 "4,202,1379" should read --4,202,879--.
At column 5, line 43 "or" should read --of--.
At column 8, line 28 "integer," should read --integer;--.
At column 9, line 5 "phenylalanint" should read --phenylalanine--.
At column 9, line 59 "he reduced" should read --be reduced--.
At column 10, line 31 "Toiletties" should read --Toiletries--.
At column 10, line 39 "stirring until" should read --stirring, until--.

UNITED STATES PATENT AND TRADEMARK OFFICE
CERTIFICATE OF CORRECTION

PATENT NO. : 5,641,476
DATED : June 24, 1997
INVENTOR(S) : Curtis B. Motley

It is certified that error appears in the above-identified patent and that said Letters Patent is hereby corrected as shown below:

At column 11, line 1 please delete "weight of the composition.".

At column 14, line 21 "zirconia" should read --zirconium--.

At column 14, line 26 "akyl" should read --aryl--.

Signed and Sealed this

Fifth Day of May, 1998

*Attest:*

BRUCE LEHMAN

*Attesting Officer*     *Commissioner of Patents and Trademarks*